(12) United States Patent
Dunne et al.

(10) Patent No.: US 8,323,747 B2
(45) Date of Patent: Dec. 4, 2012

(54) ZEOLITE CONTAINING WASH COATS FOR ADSORBER HEAT EXCHANGERS AND TEMPERATURE CONTROLLED ADSORBERS

(75) Inventors: Stephen R. Dunne, Algonquin, IL (US); Pamela J. Dunne, legal representative, Algonquin, IL (US); Alexander M. Bershitsky, Northbrook, IL (US); Mariola J. Proszowski, Des Plaines, IL (US)

(73) Assignee: UOP LLC, Des Plaines, IL (US)

( * ) Notice: Subject to any disclaimer, the term of this patent is extended or adjusted under 35 U.S.C. 154(b) by 17 days.

(21) Appl. No.: 13/160,181

(22) Filed: Jun. 14, 2011

(65) Prior Publication Data

US 2011/0319673 A1 Dec. 29, 2011

Related U.S. Application Data

(60) Provisional application No. 61/358,448, filed on Jun. 25, 2010.

(51) Int. Cl.
*C23C 22/00* (2006.01)

(52) U.S. Cl. ........ 427/452; 556/170; 556/173; 556/450; 556/462

(58) Field of Classification Search .................. 427/452; 556/450, 462, 170, 173
See application file for complete search history.

(56) References Cited

U.S. PATENT DOCUMENTS

| | | | |
|---|---|---|---|
| 4,061,724 A | 12/1977 | Grose et al. | |
| 4,141,186 A | 2/1979 | Schoofs | |
| 4,310,440 A | 1/1982 | Wilson et al. | |
| 4,440,871 A | 4/1984 | Lok et al. | |
| 4,567,027 A | 1/1986 | Detournay et al. | |
| 4,610,700 A | 9/1986 | Miller et al. | |
| 5,120,694 A | 6/1992 | Dunne et al. | |
| 5,210,062 A | 5/1993 | Narula et al. | |
| 5,620,603 A | 4/1997 | Betz et al. | |
| 5,863,508 A | 1/1999 | Lachman et al. | |
| 6,214,303 B1 | 4/2001 | Hoke et al. | |
| 6,248,682 B1 | 6/2001 | Thompson et al. | |
| 6,500,490 B1 | 12/2002 | Yan | |
| 6,576,199 B1 | 6/2003 | Liu et al. | |
| 6,962,193 B2 | 11/2005 | Liu et al. | |
| 6,973,963 B2 | 12/2005 | Dunne et al. | |
| 7,037,878 B2 | 5/2006 | Liu et al. | |
| 7,257,942 B2 | 8/2007 | Schmeichel et al. | |
| 7,278,259 B2 | 10/2007 | Schmeichel et al. | |
| 7,278,410 B2 | 10/2007 | Hoke et al. | |
| 7,326,277 B1 | 2/2008 | Cohen et al. | |
| 7,795,479 B1 | 9/2010 | Wegerer et al. | |
| 2008/0023181 A1 | 1/2008 | Dunne et al. | |
| 2010/0132254 A1 | 6/2010 | Wegerer et al. | |
| 2010/0132548 A1 | 6/2010 | Dunne et al. | |
| 2010/0137657 A1 | 6/2010 | Wegerer et al. | |
| 2010/0150812 A1 | 6/2010 | Dunne et al. | |

FOREIGN PATENT DOCUMENTS

| | | |
|---|---|---|
| EP | 2161573 A1 | 3/2010 |
| GB | 868846 | 5/1961 |

OTHER PUBLICATIONS

Breck, "Zeolite Molecular Sieves", John Wiley & Sons, Inc., New York, 1974, pp. 633-641.
Kryl, "Catalytic Converters for Automobile Diesel Engines with Adsorption of Hydrocarbons on Zeolites", Ind. Eng. Chem. Res. 2005, 44, 9524-9534.
Silver, "A Durable In-Line Hydrocarbon Adsorber for Reduced Cold Start Exhaust Emissions", SAE Special Publications, v 1296, Oct. 1997, reprinted from Topics in General and Advanced Emissions. Conference: International Fall Fuels & Lubricants Meeting & Exposition, Oct. 13-16, 1997, Tulsa, OK, USA.

*Primary Examiner* — Elvis O Price
(74) *Attorney, Agent, or Firm* — Mark Goldberg

(57) ABSTRACT

The present invention provides a process for applying a coating on a heat exchanger or a temperature controlled adsorber surface. This coating comprises a zeolite, an organic solvent, an organic siloxane resin that constitutes a binder and a plasticizing agent.

11 Claims, No Drawings

ZEOLITE CONTAINING WASH COATS FOR ADSORBER HEAT EXCHANGERS AND TEMPERATURE CONTROLLED ADSORBERS

CROSS-REFERENCE TO RELATED APPLICATION

This application claims priority from Provisional Application No. 61/358,448 filed Jun. 25, 2010, the contents of which are hereby incorporated by reference.

BACKGROUND OF THE INVENTION

The present invention relates to improved coatings and a method of applying these coatings to adsorption heat exchangers and temperature controlled adsorbers. In particular, the present invention provides for a method of providing thin adsorbent coatings that allow for much higher operating efficiency, greater heat transfer capacity and more effective functionality than prior art adsorbent packed beds.

There are a variety of solid adsorbents which have been useful in adsorption and catalysis including commonly known materials such as activated carbons, activated clays, silica gel, activated alumina, and crystalline molecular sieves. Of these adsorbents, crystalline molecular sieves such as silicoaluminophosphates, aluminophosphates and aluminosilicate zeolites have been particularly useful because of their uniform pore size.

In many instances it is desirable to have the solid adsorbent deposited on a substrate as a coating instead of being contained in particulate form as pellets, beads, or other particles. There are several reasons why solid adsorbent coatings have been used including, for example, to improve the catalytic or adsorption properties of the solid adsorbent by improving the surface area to weight ratio, to reduce pressure drop, to enhance mass transfer rates, to reduce the amount of solid adsorbent required, to protect the underlying substrate material from a harmful environment, to achieve a particular strength or form, and, to perform the particular adsorptive or catalytic function over the entire coated surface of the substrate.

Not surprisingly, there has been a diversity of end users for solid adsorbent coatings. Moreover, the methods for applying the coatings have been varied and somewhat dependent on the particular end use. The use of adsorption heat exchangers was disclosed in US 2008/0023181 A1. In that invention, a metal substrate is coated with an adsorptive material coating in accordance with U.S. Pat. No. 5,120,694 which taught the use of ceramic binders together with zeolite and other adsorbents as the coating material that are applied in a water based slurry. These prior art heat exchangers contain high quality adsorbent layers but these materials provide an intrinsic limit where it is not possible to have a density of fins more than about 197 to 276 fins per linear meter (5 to 7 fins per linear inch). Increased density of fins is desirable in providing for increased mass transfer.

U.S. Pat. No. 6,576,199 discloses the manufacture of an aircraft environmental control system in which a metal catalyst is placed upon a catalytic converter with a wash coat that contains an organic siloxane resin. This is a very thin layer that is provided to enhance catalytic activity as compared to the present invention where adsorption and effective heat transfer are the result of providing the layer of adsorbent material on the substrate.

Whereas the ceramic structure of the prior art does promote good mass transfer the art taught here imparts superior mass transfer due to the framework structure that is formed with the inorganic component ($SiO_2$) that is left behind after the curing and calcination of the organosiloxane resin. We further anticipate the need to coat and the ability to coat substantially larger adsorption heat exchangers and teach methods whereby the coating can be applied to large heat exchangers which could not be dip coated via the means taught in prior art.

Adsorption heat exchangers or temperature controlled adsorbers can achieve much higher operating efficiency, greater heat transfer capacity and more effective functionality as both an adsorber and a heat exchanger if the adsorbent is applied as a coating on the heat exchanger surface rather than by including the adsorbent as a "packed bed" of beads, pellets or granules of adsorbent material.

SUMMARY OF THE INVENTION

The process of the present invention provides a process for the coating of adsorber heat exchangers and temperature controlled adsorbers wherein the process includes the following steps: (1) slurry preparation; (2) slurry viscosity monitoring and adjustment; (3) metal surface preparation; (4) slurry application; (5) removal of excess non adhered slurry (air knifing); (6) weight check; (7) calcination of organic content of the applied coating; and (8) a repetition of steps (4) through (7) until a targeted thickness of the coating has been achieved. In particular, the present invention provides adsorbent-substrate composites wherein solid adsorbents are bonded to aluminum substrates. These composites can have coatings that have improved adsorption properties over pelleted or beaded adsorbent particles as well as excellent physical and thermal cycling properties.

DETAILED DESCRIPTION OF THE INVENTION

The present invention provides methods of coating a surface of an substrate such as a polymer composite, aluminum, aluminum ceramic, copper, titanium, brass, stainless steel, and graphite fiber composite materials with a layer of solid adsorbent which includes the steps of contacting the surface with a slurry comprising the solid adsorbent and a binder in a suspending liquid to form a slurry-coated surface, and removing sufficient liquid to form a coating thereon. In a preferred aspect, the coated surface is additionally heated to a temperature and for a period of time sufficient to cause hardening thereof, wherein the temperature is at least 200° C., preferably between about 400° and 650° C., and the period of time for heating is at least 0.25 hours and preferably about 1 hour. Other preferred aspects involve utilizing, as the solid adsorbent, crystalline molecular sieves, more preferably zeolites, and most preferably Zeolite A, Zeolite X, Zeolite Y, Chabazite and mixtures thereof.

A particularly preferred aspect of the present invention provides a method of coating surface of an aluminum substrate with a layer of molecular sieve which includes the steps of contacting the surface with a slurry having solid materials containing about 60 to 95 wt-% molecular sieve and about 5 to 40 wt-% binder, the solid materials comprising about 10 to 40 wt-%, preferably about 30 wt-% of the total weight of the slurry with the balance comprising a suspending liquid, to form a slurry-coated surface, and heating the slurry-coated surface to a temperature of about 550° to 650° C. for about 1 hour to remove sufficient liquid to form a coating thereon and cause hardening thereof.

The layered adsorbent-substrate composites produced by the method of the present invention can have improved adsorption properties over pelleted or beaded adsorbent particles. The slurry preparation must include a zeolite as the key active ingredient; an organic solvent to form the slurry; an organic siloxane resin that constitutes the binder; and a plasticizing agent. The target coating layer is in the range of 0.1 to 1 mm and more preferably about 0.3 to 0.5 mm in thickness. It is anticipated that multiple coating passes are needed to achieve the target. Adjustment of the slurry solids content alters not only the viscosity of the slurry but also the added thickness for each subsequent slurry application. The means of adjusting the solids content and viscosity are known. The zeolite is chosen to perform the adsorptive separation that is desired for the coated adsorber heat exchanger and it may be selected from almost any of the known zeolite structures including zeolite Types A, X, and Y, Chabazite, Mordenite, UZM-5, silicalite and other higher silica structures. The organic solvent must be selected for its solvating ability and a low surface tension so as to allow the coating of closely spaced heat exchanger surfaces (e.g. high values of the fin density). The organic siloxane resin will be chosen to provide easy application and then allow for a residual that is essentially pure $SiO_2$.

One example of the slurry preparation has the following composition: 67 grams of zeolite (herein DDZ-70); 100 grams of toluene as the organic solvent; 70 grams of organosiloxane resin (here GE's SRP-500) and about 60 drops of zinc octoate to act as a plasticizing agent. The slurry must be continuously agitated to prevent settling of the solids. The application of the slurry may be by dipping a part into a slurry bath or by flooding a given heat exchanger with the slurry or by a similar method. Removal or draining of the slurry will leave behind an adhered layer of slurry and some unadhered slurry. Air-knifing removes that portion of the slurry not adhered to the heat exchanger surface.

The calcination step is vital and involves a ramp in temperature from ambient to calcination temperature (450° to 600° C., more preferably 550° to 600° C.). The ramp rate must be controlled to prevent cracking of the coating. A minimum hold at top temperature for 30 minutes and more preferably 1 hour, followed by a controlled cooling step. The air flow during the calcination must be sufficient to promote complete combustion of the organic species contained in the coating. Carbon residues in the coating are detrimental to capacity and mass transfer properties of the wash coated layer.

The following detailed description is of one of the currently contemplated modes of carrying out the invention. The description is not to be taken in a limiting sense, but is made merely for the purpose of illustrating the general principles of the invention, since the scope of the invention is best defined by the appended claims.

Broadly, the present invention provides adsorption heat exchangers for adsorption heat pumps and adsorption applications. Embodiments of these exchangers are not in themselves intended to promote heat transfer in a general sense, rather they are intended to enhance the transport of sensible heat to or from a heat transfer fluid into or out of the adsorbent coating applied in a plurality of adsorbent layers, these exchangers are thus efficient at adsorbing and desorbing a working fluid such as water, and methods for using the same. Embodiments of the present invention may find beneficial use in industries such as the automotive, electricity generation and aerospace industries. Embodiments of the present invention may be useful in applications including adsorption refrigeration systems, adsorption based air conditioning systems and environmental control systems. Embodiments of the present invention may be useful in any heat transport application where in it is desired to efficiently heat or cool an adsorbent mass to promote adsorption or desorption of a working fluid. Such adsorbent heat exchangers may find use in applications including, but not limited to, heat transport for automobile air conditioning systems.

In one embodiment, the present invention provides an adsorption heat exchanger having a stack of alternating adsorption layers and heat transfer layers. The adsorption heat exchanger can comprise a stack of alternating corrugated sheets and separator plates. The corrugated sheets can be oriented in an alternating manner to provide an adsorption flow path in one direction and a heat transfer flow path in another direction (about 90 degrees to the adsorption flow path). The surfaces defining the adsorption flow path can be coated with an adsorptive material. Unlike the prior art tube-lamellas design, the present invention can comprise a plate-corrugated sheet-plate design. For some embodiments, the plate-corrugated sheet-plate design allows for enhanced primary surface area and more efficient heat and mass transfer.

Unlike the prior art that includes adsorptive paper laminates, the adsorptive material of the present invention can be applied directly to a brazed heat exchanger assembly, reducing production time. Additionally, the adsorptive material coating of the present invention can provide a reduction in coating thickness and attendant enhancement of both heat and mass transfer.

Moreover, unlike the prior art wherein the heat transfer fluid flow path comprises a tube, the heat transfer fluid flow path of the present invention can include a corrugated sheet that extends between and in contact with two separator plates. The corrugated sheet can form a plurality of fins running parallel to the flow of heat transfer fluid. The fins can increase heat transfer to the adsorption layer without adversely affecting the flow of the heat transfer fluid.

Embodiments of the present invention may include an adsorption heat exchanger designed to thermally connect with a sorptive cooling system. The sorptive cooling system can include an adsorption heat exchanger, a condenser and an evaporator. The adsorption heat exchanger can be operationally connected to a heat transfer fluid loop and an adsorption loop.

During operation of the sorptive cooling system, heat from a flow of heat transfer fluid flowing through the heat transfer fluid loop can heat exchange with an adsorptive material coating and drive a flow of adsorbate (e.g. a refrigerant) flowing through the adsorption loop. As the adsorptive material coating is heated, the flow of adsorbate is caused to move toward the condenser. The flow of adsorbate is desorbed from the adsorptive material coating within the adsorption heat exchanger, driving adsorbate vapor to the condenser. In the condenser, the adsorbate vapor can be cooled and condensed. The adsorbate condensate can then pass to the evaporator where the adsorbate condensate can be heat exchanged with a process stream or space to be conditioned to revaporize the adsorbate condensate.

When further heating of the adsorptive material coating no longer produces desorbed adsorbate from the adsorptive material coating, the adsorption heat exchanger can be isolated and allowed to return to the adsorption conditions. When the adsorption conditions are established in the adsorptive material coating, the adsorbate vapor from the evaporator can be reintroduced to the adsorption heat exchanger to complete the cycle. Generally, two or more adsorption heat exchangers may be employed in a typical cycle wherein one adsorption heat exchanger is heated during the desorption stroke and a second adsorption heat exchanger is cooled during the adsorption stroke. The time for the completion of a full cycle of adsorption and desorption is known as the "cycle time."

The density of adsorption zone fins (fins/meter) may vary with application and may depend on factors including the thickness of the adsorptive material coating 46 and the desired volume of the adsorption flow passage. The density of the adsorption zone fins may be defined as the number of fins per meter of adsorption layer width as measured perpendicular to the adsorption flow line and parallel to the separator plate. For some applications, the density of the adsorption zone fins may be between about 276 and about 1102 fins/meter (7 and 28 fins/inch).

The adsorption zone contact portions may be positioned about parallel to and in contact with the separator plates. The adsorption zone contact portions may be brazed to an adsorption zone facing side of the separator plates. The adsorption zone contact portions may provide a support for at least a portion of the adsorptive material coating. In other words, one side of the adsorption zone contact portion may be brazed to the separator plate and the other side may be coated with the adsorptive material coating. For some applications, the adsorption zone contact portions may have an adsorption contact portion width of between about 0.89 and about 3.81 mm (0.035 and 0.15 inch). The adsorption contact width is not an independent parameter. Once the density of the adsorption zone fins and the adsorption fin thickness have been specified the adsorption contact width is a determinate value. The adsorption contact portion width may vary and may depend on the desired density of the adsorption zone fins. The adsorption contact portion width may be inversely proportion to the density of the adsorption zone fins.

The present invention provides adsorbent-substrate composites and methods for preparing the composites by coating an aluminum substrate with a layer of solid adsorbent, preferably molecular sieve, and more preferably zeolite. Other aspects of the present invention relate to process for utilizing the adsorbent coatings.

The substrates used in the present invention provide structural support for the solid adsorbent layer as well as provide a suitable bonding medium for the solid adsorbent and binder. The substrate may be, for example, aluminum metal, aluminized steel, aluminized ceramic and other similar materials. The substrate may be in various forms including, but not limited to, sheets, foils, tubes, wires, plates, balls, bars, chains, mesh or particles. It is not necessary for the aluminum substrate to be chemically treated or washed with solvent in order to practice the present invention, however the substrate should be relatively free from large amounts of foreign matter which may adversely affect bonding, such as dirt or grease.

Virtually any synthetic or naturally occurring solid adsorbent capable of maintaining its physical integrity during the coating process is suitable for use according to the present invention. The selection of the particular solid adsorbent will depend on factors such as its effective pore diameter and the particular end use intended. The term "effective pore diameter" is conventional in the art and is used herein to functionally define the pore size in terms of the size of molecules that can enter the pores rather than actual dimensions which are often difficult to determine as the pores are often irregularly shaped, i.e., non-circular. D. W. Breck, in ZEOLITE MOLECULAR SIEVES, John Wiley and Sons, New York, 1974, at pages 633 to 641, provides a discussion of effective pore diameter which is hereby incorporated by reference.

Although there are a variety of solid adsorbents which are suitable for use according to the present invention including but not limited to activated carbons, activated clays, silica gel, activated alumina and crystalline molecular sieves, molecular sieves are preferred for adsorption and catalysis because of their uniform pore size, i.e., effective pore diameter. These molecular sieves include, for example, the various forms of silicoaluminophosphates, and aluminophosphates disclosed in U.S. Pat. No. 4,440,871, U.S. Pat. No. 4,310,440 and U.S. Pat. No. 4,567,027, hereby incorporated by reference, as well as zeolitic molecular sieves.

Typical well known zeolites which may be used include, chabazite, also referred to as Zeolite D, clinoptilolite, erionite, faujasite, also referred to as Zeolite X and Zeolite Y, ferrierite, mordenite, Zeolite A, and Zeolite P. Detailed descriptions of the above-identified zeolites, as well as others, may be found in D. W. Breck, ZEOLITE MOLECULAR SIEVES, John Wiley and Sons, New York, 1974, hereby incorporated by reference. Other zeolites suitable for use according to the present invention are those having a high silica content, i.e. those having silica to alumina ratios greater than 10 and typically greater than 100. One such high silica zeolite is silicalite, as the term used herein includes both the silicapolymorph disclosed in U.S. Pat. No. 4,061,724 and also the F-silicalite disclosed in U.S. Pat. No. 4,104,294, hereby incorporated by reference.

The mineral chabazite (also heretofore denominated as Acadialite, Haydenite, Phacolite and Glottalite) is a widely-occurring zeolite found in Ireland, Nova Scotia and Colorado, USA, among other places and has a typical unit cell content of $Ca_2[(AlO_2)_4(SiO_2)_8]13H_2O$. It is the preferred chabazite-type zeolite for this use. Synthetic forms of the chabazite-type structure are also known, notably Zeolite D, whose synthesis and structure are described in detail in GB 868,846 A.

The faujasite-type of crystalline zeolite is represented principally by the well-known synthetic Zeolite X and Zeolite Y. At present no significant deposits of the mineral faujasite are known to exist. Zeolite X has a maximum molar $SiO_2/Al_2O_3$ ratio of 3, and accordingly does not possess a very substantial resistance toward structural degradation by acid attack. Zeolite Y and its myriad of modified forms can have molar $SiO_2/Al_2O_3$ ratios of greater than 3 up to several hundred. Preferably, a zeolite Y having a molar $SiO_2/Al_2O_3$ ratio of from 4 to 20 is employed for this use.

For purposes of the present invention, it is required that the solid adsorbent be agglomerated with a binder in order to ensure that the coating will have suitable physical properties. According to the present invention the substrate is coated with the solid adsorbent by contacting the surface of the substrate, after heating the surface as hereinafter described, with a slurry comprising the solid adsorbent and binder. The solid particles used in the slurry including both the solid adsorbent and binder material may be of any size functionally suitable in the present invention. However, the solid adsorbent and binder are desirably present as small particles, preferably having a particle size of about 1 to 500 microns, more preferably from about 1 to 50 microns.

If necessary, the solid particles may be subjected to mechanical size reduction, e.g., grinding, crushing, milling and the like, in order to obtain the desired particle size. However, it is preferred that the solid particles be more smooth, and more preferably also more spherical, relative to solid particles of similar composition obtained by mechanical size reduction. Such particle smoothness and sphericity tends to improve evenness of the coating and may also allow increased solids loading in the slurry, if desired. One particularly useful processing step to achieve such smoothness and sphericity is to employ spray drying as part of the particle manufacturing process to form the solid particles or precursors of the solid particles. An additional advantage of employing such spray drying is that the conditions of such step can be controlled so that the product solid particles are of a desired particle size or size range. The use of spray drying in such solid particle manufacturing is conventional and well known, and therefore need not be discussed in detail here. It is to be understood that the solid adsorbent and binder may be agglomerated and subjected to size reduction prior to forming the slurry, if desired.

The solid adsorbent and binder may be mixed in the slurry in a variety of proportions, whether as segregated or agglomerated particles, although it is generally desirable to use only as much binder as is required to give sufficient strength to the coated surface. It is preferred that the adsorbent portion comprises about 60 to 95 wt-% of the total weight of solids, i.e., adsorbent and binder, in the slurry and that the remaining 5 to 40 wt-% comprises binder. In addition to the adsorbent and binder, the slurry may contain a dispersing agent or surfactant to aid in suspending the particles or vary the viscosity of the slurry. Suitable surfactants include for example, Dispex, a salt of a polymeric carboxylic acid available from Allied Colloids, Suffolk, Va., and TSPP, a tetrasodium pyrophosphate available from Monsanto, St. Louis, Mo. When a surfactant or dispersing agent is used, it is preferred that its concentration be in the range of about 0.5 to 5.0 wt-% of the solids content of the slurry.

While it can be appreciated that the solid adsorbent and binder can be suspended in a dry slurry, i.e., fluidized bed, it is desirable in accordance with the present invention that the slurry contain a suspending liquid. The suspending liquid should be one which is not likely to chemically react, e.g., by itself or with the aluminum substrate or other components in the slurry. More preferably, the suspending liquid should be substantially non-reactive, should not interfere with the internal pores of the solid adsorbent and should be compatible with the organosiloxane binder. An organic solvent such as toluene is a preferred suspending liquid for use according to the present invention. The proportion of suspending liquid can be varied to adjust the viscosity of the slurry and hence, the thickness of the coating. The determination of the appropriate proportions to achieve the desired coating thickness can be made experimentally by measuring the thickness resulting from a given slurry and then either increasing the solids proportion, i.e. higher viscosity, to obtain a thicker coating, or decreasing the solid proportion, i.e., lower viscosity, to obtain a thinner coating. One way to determine the thickness of the coating is to calculate the area density coverage, i.e., the weight of solid adsorbent per unit area, and then divide by the density of the solid adsorbent. It is generally preferred that the solid materials comprise about 10 to 40 wt-%, and preferably about 30 wt-% of the total weight of the slurry, with the balance preferably consisting essentially of the suspending liquid and any surfactants or dispersing agents.

The surface is then contacted with the slurry, preferably by dipping the surface into the slurry or by spraying the slurry onto the surface, to form a slurry-coated surface. If, after the initial contacting, it is desired to increase the thickness of the coating, additional contacting steps can be performed. When such additional contacting is performed, it is not necessary to reheat the substrate.

The slurry-coated surface can then simply be allowed to dry or otherwise treated, e.g., by heating at an elevated temperature, to remove sufficient liquid to form the coating, a preferred method further comprises a heating step where the adsorbent coated surface is ramped up to a temperature of 100° to 130° C. and then remaining at that temperature for 20 to 40 minutes. Then the temperature is ramped up to 400° to 600° C. and remaining at that temperature for 30 to 90 minutes to calcine the coating. After this calcination heating step, the coating is cooled in a controlled cooling step. When this heating step is performed, it is not necessary to perform a separate liquid removal step, e.g. drying, since during the additional heating step sufficient liquid can be removed from the slurry-coated surface to form a coating thereon, as well as to cause hardening thereof. The time required to cause hardening of the coated surface is desirably at least 15 minutes and preferably about 1 hour. The calcination results in the complete oxidation of organic species within the coating.

The resulting adsorbent-substrate composite comprises an underlying aluminum substrate layer and an outer layer bonded to the surface of the aluminum substrate consisting essentially of adsorbent and residual (not original) binder. These coatings provide a high surface area as well as a minimum diffusion path for the components adsorbed on the adsorbent and hence, superior rates of adsorption compared to pelleted or beaded forms of adsorbent. Moreover, the adsorbent coatings have excellent physical durability and are resistant to chipping and flaking Furthermore, despite differences in the thermal expansion properties between the adsorbent and the aluminum substrate, the adsorbent coatings of the present invention advantageously retain their physical integrity even after repeated thermal cycling.

Another aspect of the present invention relates to processes for utilizing the adsorbent substrate composites. It can be appreciated that an adsorbent coated aluminum substrate prepared by the method of the present invention will have many uses particularly in processes for separating at least one molecular species from a mixture thereof with at least one other molecular species by means of selective adsorption. The adsorbent coated substrate may be used as a heat exchanger or temperature controlled adsorber and may be fabricated into an adsorbent wheel as described in U.S. Pat. No. 6,973,963, incorporated by reference herein in its entirety. Such adsorbent wheels may be used in brake air drying such as described in U.S. Pat. No. 7,326,277, incorporated by reference herein in its entirety. Some useful applications for the heat exchangers or temperature controlled adsorbers include the dehydration of liquids, including the dehydration of ethanol as described in US 2010/0132548 A1, US 2010/0132254 A1, US 2010/0137657 A1, US 2010/0150812 A1 and U.S. Pat. No. 7,795,479, each incorporated by reference by their entireties herein. The heat exchangers of the present invention may be used in sorption cooling and heating applications such as described in U.S. Pat. No. 6,973,963, incorporated by reference herein in its entirety.

For example, above-identified U.S. Pat. No. 4,610,700, hereby incorporated by reference, relates to adsorbent compositions used in conjunction with mufflers to adsorb water from exhaust gases and prevent corrosion. Although this patent discloses various ways to contain the adsorbent compositions within the muffler including the slip coating method quoted above from col. 5, lines 10-18, it does not specifically disclose or suggest the method of the present invention. The adsorption compositions of the present invention are particularly well suited for this type of application because of the excellent performance, physical and thermal cycling properties associated therewith.

As disclosed in U.S. Pat. No. 4,610,700, suitable adsorbent compositions for use in mufflers comprise a combination of a crystalline zeolite having the Chabazite crystal structure with a crystalline zeolite having a faujasite crystal structure. This combination of zeolites when utilized in the mufflers exhibits an unexpected synergism in reducing the amount of muffler corrosion.

The synergistic effect of the combination of chabazite-type and faujasite-type of zeolites in inhibiting muffler corrosion is evidenced in mixtures of the two in all proportions, but is more significantly exhibited, and hence preferred, when one of the zeolite types is present in an amount of ⅓ to 3 times the other zeolite type on an anhydrous weight basis. As used herein, the anhydrous weight of a zeolite constituent is arbitrarily defined as the weight of the zeolite after being calcined in vacuum at 300° C. for 3 hours. More preferably, the combined chabazite-type and faujasite-type zeolites constitute at least about 70 wt-% of the overall adsorbent-containing mass inserted into the inner cavity of the muffler. The remaining 30 wt-% of the mass can comprise any of several of the known zeolite binder materials such as clays, alumina or silicas.

Of the various cation forms in which the present zeolite materials can exist, it is preferred that in the faujasite-type zeolite, at least about 50 percent of the $AlO_4$ framework tetrahedra be associated with sodium cations, and that at least about 50 percent of the $AlO_4$ tetrahedra of the Chabazite-type zeolite be associated with sodium cations or calcium cations or a combination of these two cation species.

While it is preferred that both types of zeolite employed for this use be combined into the same adsorbent mass, it will be obvious to those of even routine skill in the art that a number of different arrangements are possible which achieve the desired results.

The use of an adsorbent coating comprising the above-mentioned zeolites as internal aluminum or aluminized steel muffler parts represents several improvements over other adsorbent containment methods. No bags or containers are needed to keep the adsorbent mass within the muffler. As previously noted, the thin uniform layer of adsorbent can have superior adsorption rates, i.e., water pick up rates, over beaded or pelleted adsorbents. The application of the adsorbent to the muffler parts can be controlled so that each specific muffler can be treated with the most effective amount of adsorbent for its given size and intended service. Moreover, no welding or fastening operations are required to affix the adsorbent mass in place.

Another beneficial use for the adsorbent-substrate composites is as a desiccant applied to the internal surfaces of an aluminum spacer in a multiple pane window. Multiple pane windows routinely contain adsorbents in the internal spaces to adsorb water and solvent to prevent condensation in the window which can cause poor visibility and aesthetics. The solid adsorbent is commonly held in a generally rectangular or T-shaped aluminum tube which is either perforated or not completely sealed so that the enclosed air containing water or solvent gases or mixtures thereof may have contact with the adsorbent. In accordance with the present invention, adsorbents suitable for use in multiple pane windows are applied to the internal surfaces of aluminum window spacers. The application may be performed either on the formed spacer or optionally on the aluminum strip or parts thereof before the forming process.

Multiple pane windows often contain several types of well known adsorbents including zeolites 3A, 4A, 13X and silica gel and mixtures thereof. These adsorbents are obtainable from UOP LLC, Des Plaines, Ill. One preferred adsorbent for use according to the present invention, either alone or in combination with other adsorbents, is zeolite 3A which has an effective pore diameter in the range about 3 Angstrom units, strongly and readily adsorbs water vapor but does not substantially adsorb either oxygen or nitrogen. U.S. Pat. No. 2,964,803 and U.S. Pat. No. 4,141,186 generally relate to the use of desiccants in multiple pane windows.

A variety of other applications will be found to exist for adsorbent coatings made in accordance with the present invention. For example, in the areas of cooling, refrigeration, and dehumidification, desiccants are used and often attached to desiccant wheels which rotate in and out of adsorption and regeneration zones. In accordance with the present invention, adsorbents may be applied to aluminum substrates e.g., aluminum foils, which can then be attached to the framework of the desiccant wheels.

The invention claimed is:

1. A method of coating a surface of a substrate with a layer of an organic siloxane and a zeolite which comprises preparing a slurry comprising an organic siloxane, said zeolite, an organic solvent and a plasticizing agent, continuously agitating said slurry, maintaining said slurry at a desired viscosity level; applying said slurry to said surface to form a layer of said organic siloxane and said zeolite, remove residual slurry, calcine said coating and repeat said application of said slurry, said removal of residual slurry and said calcining of said layer until said layer has a desired thickness.

2. The method of claim 1 wherein said substrate is selected from the group consisting of a polymer composite, aluminum, copper, titanium, brass, stainless steel, nickel, and graphite fiber composite materials.

3. The method of claim 1 wherein said coated surface is heated to a temperature of about 100° to 130° C. for about 20 to 40 minutes.

4. The method of claim 1 wherein said calcining of said coating is at a temperature that is ramped from ambient to a peak temperature of about 450° to 600° C.

5. The method of claim 1 wherein said calcining of said coating is at a temperature that is ramped from ambient to a peak temperature of about 550° to 600° C.

6. The method of claim 1 wherein said layer is between 0.1 and 1 mm thick.

7. The method of claim 1 wherein said layer is between 0.3 and 0.5 mm thick.

8. The method of claim 1 wherein said zeolite is selected from the group consisting of zeolite type A, zeolite type X, zeolite type Y, Chabazite, Mordenite, UZM-5 and silicalite.

9. The method of claim 1 wherein calcining is maintained at said peak temperature for about 30 to 90 minutes.

10. The method of claim 1 wherein after said calcining of said coating is maintained at said peak temperature, said coating is cooled in a controlled cooling step.

11. The method of claim 1 wherein during said calcination complete combustion of organic species within said coating take place.

* * * * *